United States Patent [19]

Haining

[11] Patent Number: 5,330,493
[45] Date of Patent: Jul. 19, 1994

[54] DISPOSABLE SCALPEL

[76] Inventor: Michael L. Haining, 6731 Ashmore, Houston, Tex. 77069

[21] Appl. No.: 982,596

[22] Filed: Nov. 27, 1992

[51] Int. Cl.⁵ .............................................. A61B 17/32
[52] U.S. Cl. ...................................... 606/167; 30/151; 30/335
[58] Field of Search ....................... 30/1, 51, 151, 155, 30/159, 160, 161, 162, 272.1, 286, 346; 606/167, 170, 172, 181, 182, 171

[56] References Cited

U.S. PATENT DOCUMENTS

| | | | |
|---|---|---|---|
| 3,706,106 | 12/1972 | Leopoldi | 606/167 |
| 3,906,626 | 9/1975 | Riuli | 30/162 |
| 4,735,202 | 4/1988 | Williams | 606/167 |
| 5,201,748 | 4/1993 | Newman et al. | 606/167 |
| 5,207,696 | 5/1993 | Matwijcow | 606/167 |

*Primary Examiner*—C. Fred Rosenbaum
*Assistant Examiner*—N. Kent Gring
*Attorney, Agent, or Firm*—Richard L. Moseley

[57] ABSTRACT

There is provided a disposable scalpel having a retractable blade. The blade may be secured in any of three positions: 1) an intermediated retracted position for shipping, 2) an exposed position for use and 3) a permanently locked retracted position. A cap is provided to cover the openings on the scalpel after the blade is secured in the permanently locked position.

3 Claims, 2 Drawing Sheets

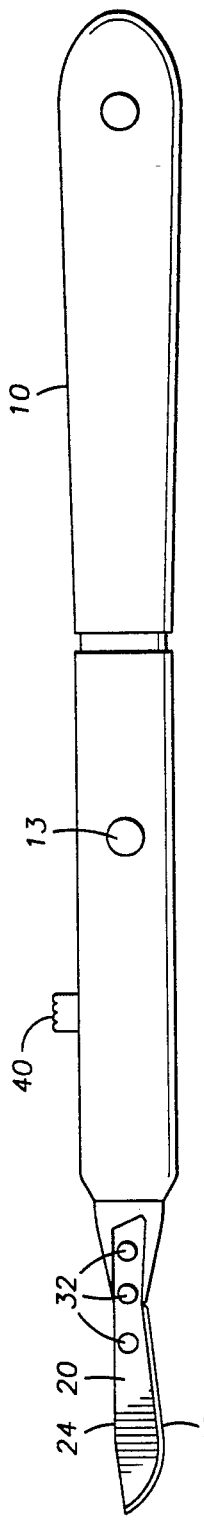
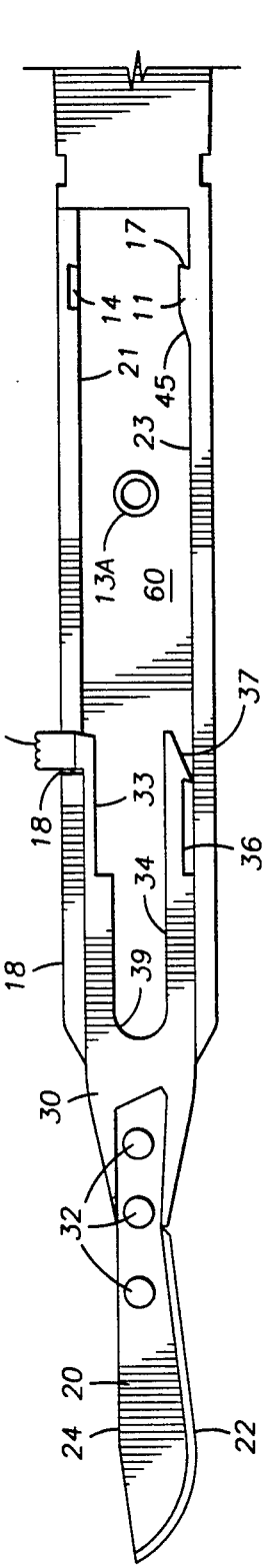
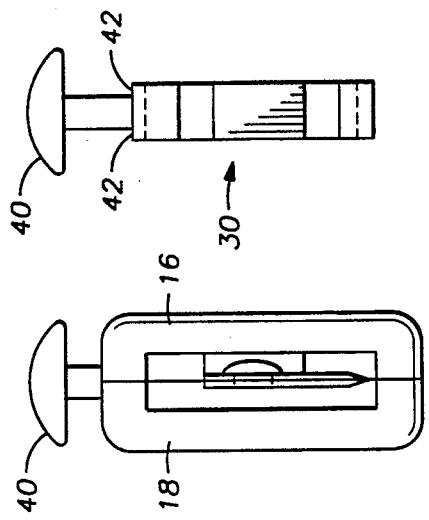
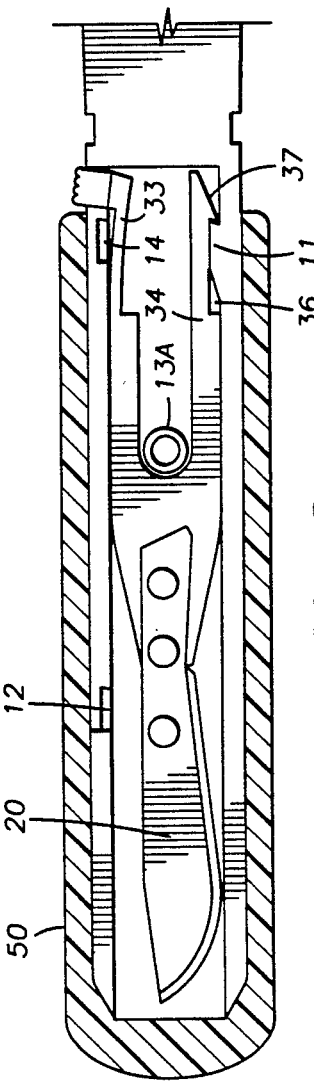
FIG. 1   FIG. 2   FIG. 3   FIG. 4   FIG. 5

DISPOSABLE SCALPEL

BACKGROUND OF THE INVENTION

1. Field of the Invention

The present invention relates generally to surgical knives and more particularly to disposable scalpels. Most particularly the invention relates to a disposable scalpel which may be retracted into the handle for safe disposal.

2. Related Art

Surgical scalpels are special knives, the blades of which are manufactured to precise standards of high quality materials. For various reasons, it has become common to use a scalpel blade only once. Therefore there are several combination handle/replaceable blade scalpels disclosed in the art. Additionally there are now available completely disposable scalpels having inexpensive plastic handles secured to the scalpel blade.

With the advent of the AIDS virus, there has now arisen much concern about transmission of disease by contact with contaminated blood. Sharp instruments, such as scalpels, which routinely come into contact with body fluids, are particularly worrisome. For this reason scalpels have been provided with removable guards to prevent contact with the blade when not in use. See for example U.S. Pat. 4,735,202 which discloses a scalpel in which the glade guard is provided in the form of a sleeve which is slidably mounted over the scalpel and may be locked into position over the blade when not in use. The blade guard requires two hands to position. Additionally U.S. Pat. No. 5,139,507 discloses such a scalpel whose guard may be easily moved into or out of position by the surgeon during actual surgery to prevent accidental cutting or jabbing when passing the instrument back and forth during surgery.

Most retractable blade guards have the disadvantage of being open at one end to allow passage of the blade. Such opening can allow any body fluids left on the blade to seep out and come into contact with either operating room personnel or clean up personnel.

After any "disposable" scalpel or blade is used there is still the problem of disposing of it. The scalpels or blades must be placed in special "sharps" containers to prevent janitorial or other clean up personnel from coming into contact with the contaminated instruments. Even if the blade is covered by a guard or sheath, there is a chance that the guard might become retracted or removed. Additionally, there is always the temptation to reuse such instruments, especially in poorer areas where disposal of a "perfectly good scalpel" might appear as a waste.

Broadly it is an object of the present invention to provide a scalpel with a retractable blade such that the blade can be positioned for use and retracted into the handle after use.

It is another object of the invention to provide a retractable blade scalpel that when fully retracted is permanently locked in the retractable position to prevent accidental reopening or reuse.

It is a further object of the invention to provide a closed container after retraction of the blade for safe disposal of the scalpel.

SUMMARY OF THE INVENTION

To achieve the above objects a scalpel is provided with a blade that is retractable into the handle. The blade may be positioned in three locations within the handle: 1) retracted for shipment, 2) exposed for use and 3) fully retracted and locked for disposal. The scalpel is shipped with a cap over the end which may be placed over the end after final retraction to provide a closed container for disposal.

More particularly the retractable blade scalpel comprises (a) a handle defining a chamber with an opening at the distal end, and having a slot through the upper surface and notches in said chamber near either end of said slot;

(b) a projection on the lower surface of said chamber near the proximal end;

(c) a blade carrier slidably mounted within said chamber;

(d) a surgical blade secured on said blade carrier oriented toward said opening;

(e) an upper flexible member extending from said blade carrier having a tab at the proximal end to engage either said notches to secure said blade in an exposed position or retracted position; and (f) a lower flexible member extending from said blade carrier having a notch on the under surface engageable with said projection to permanently lock said carrier and blade in a retracted position.

BRIEF DESCRIPTION OF THE DRAWING

FIG. 1 is a side view of a retractable blade scalpel with the blade exposed.

FIG. 2 is a side view the scalpel of FIG. 1 with one of the sides removed to expose the inner parts.

FIG. 3 is side view in partial cross section showing the blade retracted and locked in position and the cap over the end.

FIG. 4 is a front view of the scalpel shown in FIG. 1.

FIG. 5 is a rear view of the blade carrier that slides within the handle.

DESCRIPTION OF THE PREFERRED EMBODIMENT

Figure 6:
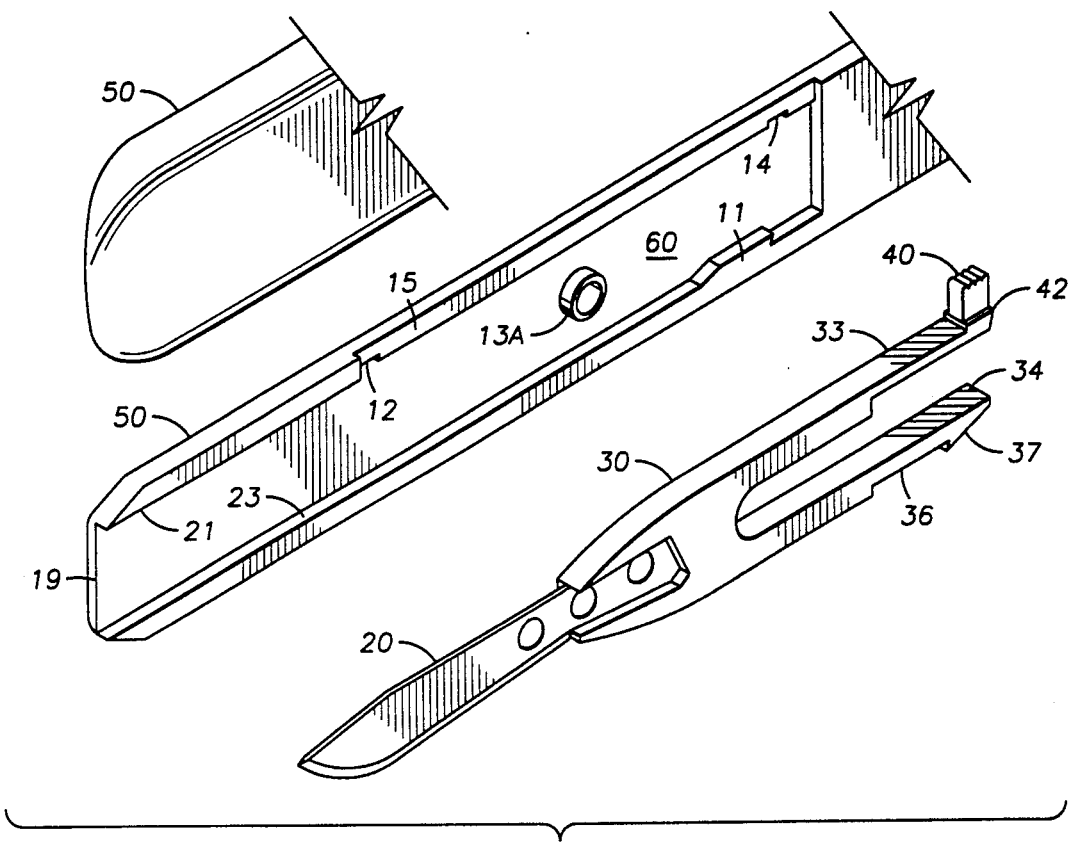
FIG. 6 is an exploded view showing one side of the handle, the blade and carrier, and the cap.

For a detailed description of the preferred embodiment the reader is directed to the accompanying figures in which like components are given like numerals for ease of reference.

Looking first to FIGS. 1–6 there is shown a scalpel having a handle 10 of two mirror image side members 16 and 18 which are held together by pin 13. A blade 20 is secured on a blade carrier 30 as by rivets 32. The blade as shown has a cutting surface 22 and a dull top surface 24. The two side members 16 and 18 when fastened together define a chamber 60 in which the carrier 30 is mounted. Inside of each side member at the top and bottom of the chamber 60 there are two parallel sliding surfaces 21 and 23 which support and guide upper member 33 and lower member 34 of carrier 30. Empty space 39 between members 33 and 34 fits about pin receptacle 13A which extends across chamber 60 to assist in alignment of blade 20 and carrier 30.

In the upper surface of each side member there is a slot 15 extending from near the front or distal end of the scalpel to end of chamber through which extend tab 40 which is part of upper member 33. The end of upper member 33 is flexible and biased upward against sliding surface 21. Near the front of slot 15 there is a notch 12 in sliding surface 21 to receive shoulder 42 (see FIG. 5) on tab 40 and secure carrier 30 and blade 20 in the exposed position.

On the lower sliding surface 23 there is a projection 11 near the proximal end of the chamber having a rearward sloping front 45 and a slightly rearward sloping rear 17. The end of lower blade carrier member 34 is also flexible and biased downward against lower sliding surface 23. On the under surface of lower blade carrier member 34 there is a notch 36 which is adapted to fit over projection 11, the rear of notch 36 conforming to the rear 17 of projection 11 to prevent any further movement of carrier 30 with blade 20. Sloping portion 37 on rear of lower carrier member 34 facilitates movement of lower carrier member 34 up slope 45 for locking as shown in FIG. 3. Cap 50 is placed over the end of scalpel after locking to provide a closed container for disposal. Importantly the cap 50 covers the entire length of slot 15 to prevent any body fluids from escaping there through.

Figure 7:
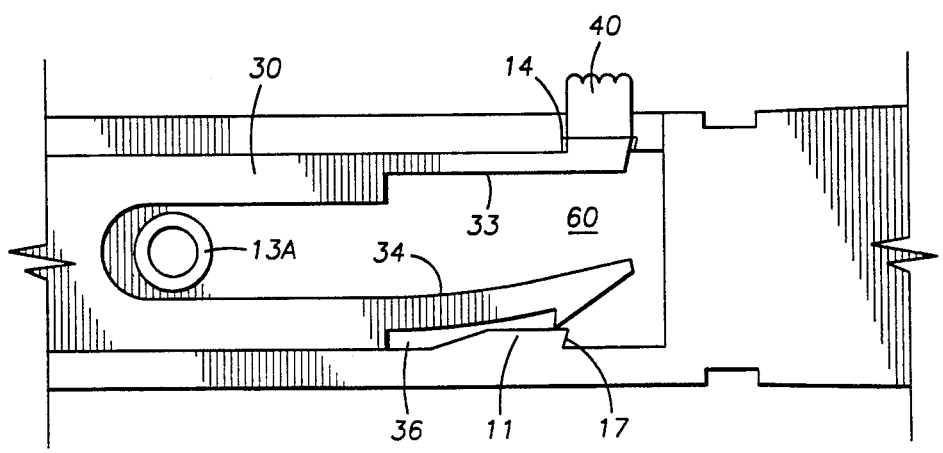
FIG. 7 is a side view showing the blade carrier in the shipping position.

Near the rear of slot 15 there is another notch 14 for securing the blade in an intermediate position for shipping. Details are shown in FIG. 7. The tap 40 engages notch 14 before notch 36 in lower carrier member 34 can engage projection 11 on lower sliding surface 23. Although not shown, the cap 50 is placed over the end of the scalpel for shipment.

It is anticipated that the scalpel will be shipped in the intermediate position with the cap covering the end. In use the cap is removed and the tab pressed down and forward until the tab engages the front notch to secure the blade in the exposed position. If at any time the surgeon wishes to lay aside the scalpel for later use on the patient, he may slide the blade back to the intermediate position. After use the tab is pressed downward and rearward until the lower carrier member engages the projection on the lower sliding surface to permanently lock the carrier inside the chamber. The only way to unlock the carrier would be to disassemble the two sides of the handle. However, in a preferred embodiment the two side members 16 and 18 are securely riveted together and disassembly would destroy the rivet.

The invention claimed is:

1. A retractable blade surgical scalpel comprising:
 (a) a handle having a proximal end and a distal end, said handle defining a chamber having an upper surface, a lower surface and an opening at the distal end, and having a slot through the upper surface and notches in said chamber near either end of said slot;
 (b) a projection on the lower surface of said chamber near the proximal end;
 (c) a blade carrier slidably mounted within said chamber;
 (d) a surgical blade secured on said blade carrier oriented toward said opening;
 (e) an upper flexible member extending from said blade carrier having a tab at the proximal end to engage either of said notches to secure said blade in an exposed position or retracted position; and
 (f) a lower flexible member extending from said blade carrier having a notch on the under surface engageable with said projection to permanently lock said carrier and blade in a retracted position.

2. The scalpel according to claim 1 further comprising a cap adapted to fit over said handle at the distal end when said carrier and blade are in the retracted position.

3. The scalpel according to claim 2 wherein said cap completely covers said slot when said carrier and blade are permanently locked in the retracted position.

* * * * *